US008974521B2

(12) United States Patent
Diener et al.

(10) Patent No.: US 8,974,521 B2
(45) Date of Patent: Mar. 10, 2015

(54) IMPLANT AND METHOD FOR MANUFACTURING SAME

(75) Inventors: Tobias Diener, Fuerth (DE); Elisabeta Burean, Erlangen (DE); Matthias Fringes, Ansbach (DE)

(73) Assignee: Biotronik AG, Buelach (CH)

( * ) Notice: Subject to any disclaimer, the term of this patent is extended or adjusted under 35 U.S.C. 154(b) by 0 days.

(21) Appl. No.: 13/369,977

(22) Filed: Feb. 9, 2012

(65) Prior Publication Data

US 2012/0220934 A1 Aug. 30, 2012

Related U.S. Application Data

(60) Provisional application No. 61/446,049, filed on Feb. 24, 2011.

(51) Int. Cl.
| | |
|---|---|
| *A61F 2/06* | (2013.01) |
| *A61L 33/00* | (2006.01) |
| *A61L 31/16* | (2006.01) |
| *A61L 31/18* | (2006.01) |
| *A61F 2/915* | (2013.01) |

(52) U.S. Cl.
CPC .............. *A61L 31/16* (2013.01); *A61L 31/18* (2013.01); *A61L 2300/606* (2013.01); *A61F 2/915* (2013.01); *A61F 2250/0068* (2013.01)
USPC .................... 623/1.42; 427/2.24; 427/2.25

(58) Field of Classification Search
USPC ......... 604/103.02; 623/1.42–1.43, 1.11, 1.15, 623/1.39–1.4; 424/422, 457; 427/2.24, 2.25
See application file for complete search history.

(56) References Cited

U.S. PATENT DOCUMENTS

| | | | |
|---|---|---|---|
| 6,540,776 B2 | 4/2003 | Sanders Millare et al. | |
| 6,896,695 B2* | 5/2005 | Mueller et al. | 623/1.15 |
| 7,060,093 B2* | 6/2006 | Dang et al. | 623/1.42 |
| 8,048,440 B2* | 11/2011 | Chang et al. | 424/423 |
| 8,070,720 B2* | 12/2011 | Johnson | 604/103.02 |
| 2009/0024210 A1* | 1/2009 | Klocke et al. | 623/1.42 |
| 2009/0030506 A1* | 1/2009 | Klocke et al. | 623/1.46 |
| 2009/0182273 A1 | 7/2009 | Johnson | |
| 2009/0198321 A1* | 8/2009 | Sutermeister et al. | 623/1.42 |
| 2010/0100169 A1* | 4/2010 | Hossainy et al. | 623/1.15 |
| 2011/0288622 A1* | 11/2011 | Chan et al. | 623/1.11 |

FOREIGN PATENT DOCUMENTS

WO 2010138726 A1 12/2010

* cited by examiner

*Primary Examiner* — Theodore Stigell
*Assistant Examiner* — Benjamin Koo
(74) *Attorney, Agent, or Firm* — Wagenknecht IP Law Group PC

(57) ABSTRACT

An implant having a preferably hollow cylindrical main structure comprising a large number of continuous openings and a coating which releases at least one pharmaceutically active substance. To attain a better distribution of the pharmaceutically active substance, at least 20% of the cross-sectional area, preferably at least 50% of the cross-sectional area, of at least a portion of the openings in a predetermined section of the main structure is covered with the coating which releases at least one pharmaceutically active substance. Furthermore, a system composed of a catheter and such an implant, a simple method for manufacturing such an implant or such a system is provided.

15 Claims, 7 Drawing Sheets

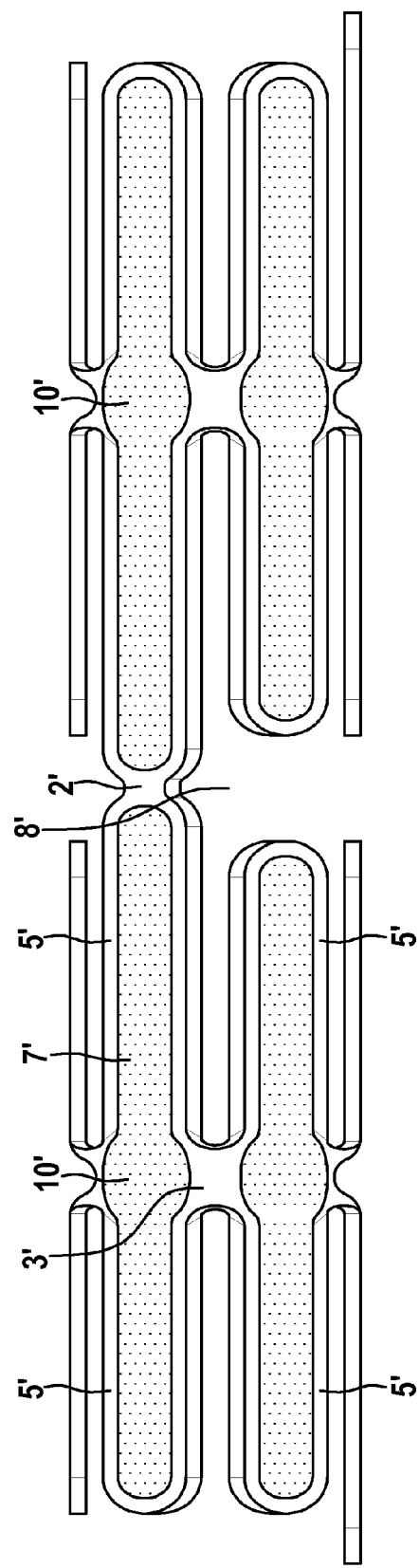

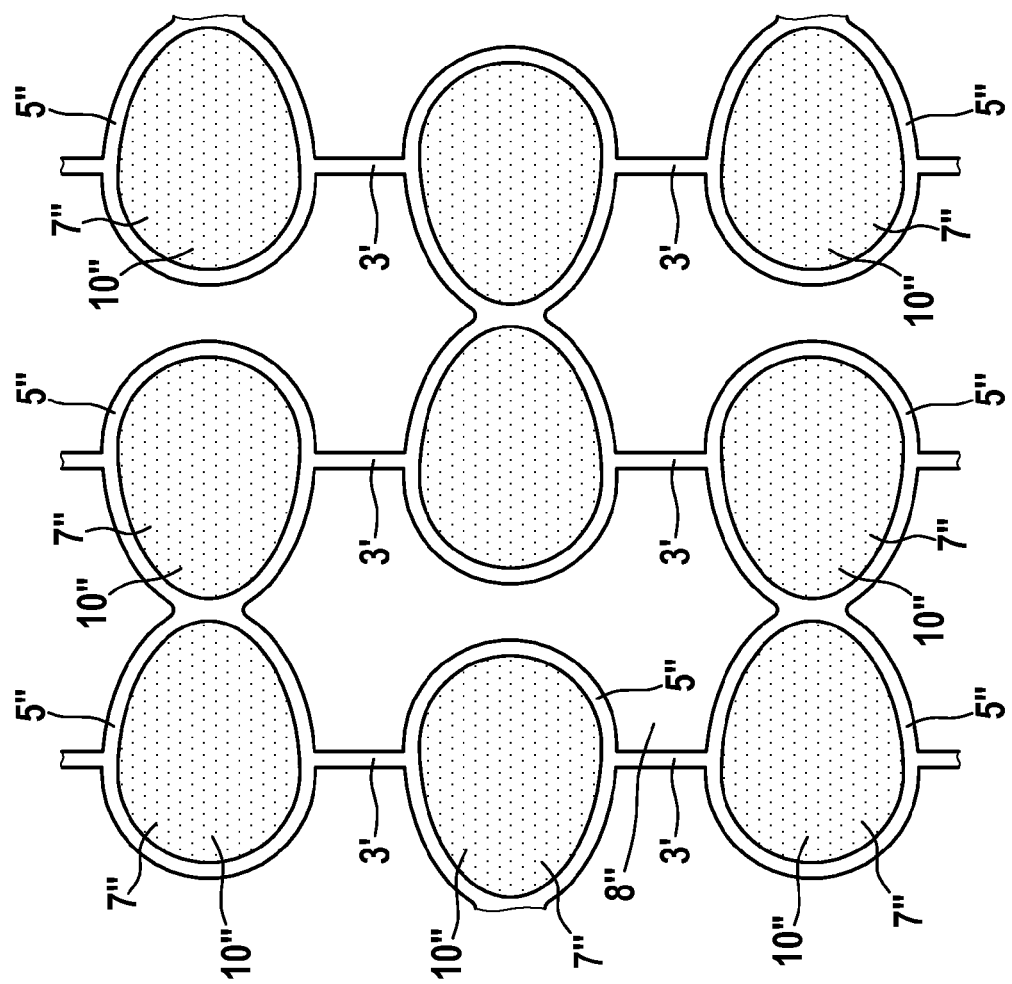

IMPLANT AND METHOD FOR MANUFACTURING SAME

CROSS REFERENCE TO RELATED APPLICATIONS

This invention claims benefit of priority to U.S. provisional patent application Ser. No. 61/446,049, filed Feb. 24, 2011; the content of which is herein incorporated by reference in its entirety.

TECHNICAL FIELD

The present invention relates to an implant, in particular an intraluminal endoprosthesis having a preferably hollow cylindrical main structure, a system composed of a catheter, and such an implant and a method for manufacturing such an implant and such a system.

BACKGROUND

A wide variety of medical endoprostheses or implants for highly diverse applications are known from the prior art. Implants according to the present invention are endovascular prostheses or other endoprostheses, such as stents (vascular stent, bile duct stent, vascular stent (including the heart and heart valve stents), mitral stent), endoprostheses for closing a patent foramen ovale (PFO), pulmonary valve stent, endoprostheses for closing an ASD (atrial septal defect), and prostheses in the region of the hard and soft tissue.

Today, stents that are used to treat stenoses (vascular constrictions) are used particularly frequently as implants. They comprise a filigree, tubular or hollow cylindrical main structure which is open at both longitudinal ends. The main structure therefore has numerous continuous openings. The main structure of the stent is often composed of individual meshes which are formed by struts having various shapes, such as zigzag or serpentine struts. Such an endoprosthesis is often inserted into the vessel to be treated using a catheter and is used to support the vessel for an extended period of time (months to years). The use of stents enables regions in the vessels to be expanded and thereby increase the lumen. Although the use of stents or other implants makes it possible to obtain an optimal vascular cross section that is necessary primarily for therapeutic success, the permanent presence of a stent—which is a foreign body after all—initiates a cascade of microbiological processes that promote e.g. inflammation of the vessel to be treated, or a necrotic change in the vessel, and/or that can result in gradual closure of the stent due to the formation of plaques or the coagulation of bodily fluid induced by a flow change or a process of infection.

To prevent restenoses, as well as inflammation and necrosis, stents or other implants are often coated with drugs that have an anticoagulant or antiinflammatory effect, for example. In that particular case it is desirable for the implants to release the pharmaceutically active substances in a targeted manner.

Stents are already known that dispense drugs from a coating which can consist of a polymer, for example. Drug depots with pumps are likewise already known. The disadvantage of the known solutions is that the pharmaceutically active substances are delivered permanently and the release cannot be controlled. In addition, the substances can only be dosed constantly, nor is it possible to determine how much of the drug is left in the reservoir or depot. The organism of the human or animal being treated is stressed unnecessarily by the permanent delivery of the contents.

Publication U.S. Pat. No. 7,060,093 B2 makes known a stent which comprises recesses (depots) in the struts. These depots contain drugs and deliver them later. The delivery of drugs from such depots is likewise difficult to control and results in an unfavorable distribution of the drug across the inner surface of the vessel being treated. This likewise results in greater stress on the organism being treated since an overdose is induced locally in order to ensure that a sufficient quantity of drug is delivered to all necessary regions of the organ being treated, which can induce toxic reactions.

SUMMARY

The problem addressed by the present invention is that of creating an implant that enables a drug to be delivered in a manner that is more targeted and places less stress on the organism. In addition, an economical system composed of an implant and a catheter is provided, as well as a method for manufacturing such an implant and such a system.

The problem described above is solved by an implant, in the case of which at least 20% of the cross-sectional area, preferably at least 50% of the cross-sectional area, of at least a portion of the openings in a predetermined section of the main structure—preferably the openings in the predetermined section having the smallest cross-sectional area—particularly preferably at most 95% of the sum of the cross-sectional areas of all openings of the predetermined section is covered or spanned in the dilated state with the coating that releases the at least one pharmaceutically active substance. The coating contains the at least one pharmaceutically active substance in pores, for example. The openings having a coating can be completely covered in the non-dilated state, e.g. in the crimped state, in which the implant is crimped onto a balloon. The coating does not break open, e.g. along a predetermined breaking point, until dilation occurs, and so a smaller portion of the cross-sectional area of the particular openings is covered in the expanded state. The behavior of the coating can be calculated in advance in a simulation using FEM analysis (finite element analysis). This can be used to adjust the properties of the coating in a targeted manner.

In regard to the present invention, the expression "cross-sectional area" refers to the area that spans the particular opening along the abluminal plane of the jacket of the implant. In other words, the cross-sectional area is the area of the opening that is visible when an observer looks at the opening from the outside. The coating extends from the main structure enclosing the particular opening into the opening and spans it in the manner of a "skin". The maximum layer thickness of the coating is preferably 100 µm.

The implant according to the invention has the advantage that a large area for the delivery of drugs is finally provided. This area is much larger than the area of the struts, for example, which are used for drug delivery in the prior art. A more even distribution of the pharmaceutically active substance over the area to be treated, e.g. the inner wall of a vessel, is therefore attained. As a result, an overdose of the pharmaceutically active substance in the region of the treated organ can be prevented, thereby ensuring that side effects such as toxic reactions do not occur.

Due to the large area that is available for delivery of the pharmaceutically active substance, luminal delivery of the pharmaceutically active substance is not necessary, either, since abluminal delivery of the pharmaceutically active substance is sufficient. According to the invention, the pharmaceutically active substance is therefore delivered from the coating at least primarily in the abluminal direction. Preferably at least 95% by weight of the at least one pharmaceutically active substance is released from the coating in the abluminal direction. This is advantageous because luminal delivery of drugs can hinder adhesion of the implant or endothelialization. Since the drug is not delivered luminally in the solution according to the invention, adequate endothelialization of the implant is ensured, and delayed thrombosis can be prevented. The at least one pharmaceutically active substance is delivered in that the pores containing the coating expand during and after dilation of the implant. The release of the at least one pharmaceutically active substance disposed in the matrix of the coating is therefore initialized or induced by the dilation of the implant. Furthermore, the opened pores of the coating can be used as a point of action for the degradation of the matrix being used, which is preferably composed of a polymer, when degradable materials are used for the coating matrix.

The pores which accommodate the pharmaceutically active substance can be provided e.g. by using a porous polymer as the coating material. As an alternative or in addition thereto, pores can be created in a mechanical way e.g. by punching. In that case, the material of the coating is initially stretched to a great extent, the pores are punched, and the material is then released. The pores are filled while the coating material is stretched. Once the filling, i.e. the pharmaceutically active substance, hardens, the coating material is released and the polymer returns to the original shape thereof. The range of expansion of plastic deformation should be avoided when the coating material is stretched as described above. This method applies for "normal" polymers as well as memory-effect polymers. Etching is another way to form pores in the coating.

Furthermore, it is possible to prepare the implant for a primarily abluminal delivery of the pharmaceutically active substance. According to one embodiment of the present invention, the coating comprises a plurality of layers, wherein the first layer, which is disposed furthest away in the luminal direction, is preferably designed as a diffusion barrier for the at least one pharmaceutically active substance. A multiple-layered coating is therefore used in this embodiment, wherein a layer that does not contain a pharmaceutically active substance is applied first. This layer, which is preferably composed of a polymer or a degradable material, is used as a diffusion barrier or diffusion block for the pharmaceutically active substance, and is disposed in the coating furthest away in the luminal direction. Once this layer has hardened, at least one more layer which contains at least one pharmaceutically active substance embedded in the matrix thereof is applied over it. The material of the matrix can also be biodegradable.

In a further embodiment, one or more predetermined breaking points (e.g. in the form of a predetermined breaking line composed of hole perforations in the coating applied along a line, or a linear reduction of the layer thickness of the coating) can be provided, which tear in a defined manner during dilation of the implant. In particular, this enables the release of the pharmaceutically active substance contained in the coating.

According to the invention, it is possible to apply the coating of the pharmaceutically active substance only on predetermined sections of the main structure, such as only on the ends of the implant in a longitudinal direction of the implant, to prevent effects such as dog boning, flow-induced proliferation at the ends of the implant, or the like. The drug, which is only delivered locally in the predetermined section of the main structure, can act in a targeted manner where it is required, and does not unnecessarily need to be disposed along the entire axis of the implant.

Since a lower concentration of the pharmaceutically active substance is required overall, the degradation of the implant—if the main structure is composed of a degradable material—will also not unnecessarily affect the pharmaceutically substance. The substance can therefore elute freely and effectively prevent restenosis.

Within the scope of the present invention, a "pharmaceutically active substance" (or therapeutically active or effective substance) is understood to mean a plant-based, animal-based, or synthetic active substance (drug) or a hormone that is used in suitable doses as a therapeutic agent to influence states or functions of the body, as a replacement for active substances that are produced naturally by human or animal bodies, such as insulin, and to eliminate or render harmless pathogens, tumors, cancer cells, or foreign substances. The release of the substance into the surroundings of the endoprosthesis has a positive effect on the healing process or counteracts pathological changes in the tissue after a surgical procedure, or serves to render diseased cells harmless in oncology.

Pharmaceutically active substances of that type typically have e.g. an antiinflammatory and/or antiproliferative and/or spasmolytic effect, thereby making it possible to prevent e.g. restenoses, inflammation, or (vascular) spasms. In particularly preferred embodiments, substances of that type can be composed of one or more substances from the active ingredient group of calcium channel blockers, lipid regulators (e.g. fibrates), immunosuppressants, calcineurin inhibitors (e.g. Tacrolimus), antiphlogistics (e.g. cortisone or dichlofenac), anti-inflammatory drugs (e.g. imidazole), antiallergenics, oligonucleotides (e.g. dODN), estrogens (e.g. genistein), endothelium formers (e.g. fibrin), steroids, analgesics, antirheumatics, proteins, hormones, insulins, cytostatic agents, peptides, vasodilators (e.g. Sartane) and the antiproliferative substances of taxols or taxanes, preferably in this case paclitaxel or sirolimus, or can be taken from the following list: Cisplatin, tirapazamine, the enzyme L-asparaginase, methotrexate, 5-fluorouracil, azathioprine, mitoxantrone, cyclophosphamide, methotrexate, natalizumab, Adriamycin PFS, Adriamycin RDF, alitretinoin, altretamine, aromasin, azathioprine, bicalutamide, busulfan, busulfex, capecitabine, casodex, cyclophosphamide, Cytoxan, Doxorubicin, exemestane, femara, finasteride, gemtuzumab, ozogamicin, Hexylen, Imuran, letrozole, Mifeprex, mifepristone, Myleran, Mylotarg, Neosar, Nolvadex, Panretin, Propecia, Proscar, Rubex, tamoxifen, Temodar, temozolomide, Trelstar Depot, triptorelin, Genasense (the company Genta), INGN201 (the company Introgen Therapeutics), SCH58500 (the company Schering-Plough), ONYX-015 (the company Onyx Pharmaceuticals), E1A-lipid complex (the company Targeted Genetics), TRAIL (the company Genentech/Immunex), GX01 (the company Gemin X Biotechnologies), cyclosporin A, DPPE, PSC 833, buthionine sulfoximine, dexverapamil, quinine, verapamil, XR9576, dexniguldipine, GF120918, lobradimil, LY335979, MS209, R-101933, gemtuzumab ozogamicin, SGN-15, MCC-465, SB-408075, A5B7 antibody against CEA with carboxy peptidase A+mustard prodrug, amifostine, dexrazoxane, BB-10010, transfer of MDR genes, BNP7787, tirapazamine, aplidine, arsenic trioxide, BMS-247550, CHS828, CT 2584, dolastatin-10, ET-743, exisulind, irofulven, KW-2189, lovastatin, E7070, LU103793, LY355703, pyrazoloacridine, TLK286, apomine, CP-461, EP0906, FB642, FK317, FK866, Kahalalide F, LAF389, PNU-166196, RO 31-7453, cetuximab (Erbitux), trastuzumab (Herceptin), ABX-EGF, AP12009, EMD55900, EMD72000, ICR62, 2A11, CCI-779, ISIS-3521, oblimersen (Genasense), OSI-774 (Tarceva), PS-341, R115777 (Zarnestra), STI571 (Gleevec), ZD1839 (Iressa), bryostatin-1, flavopiridol, GD0039, GEM231, ilmofosine, ISIS-2503, ISIS-5132, L-778 123, PKC 412, SCH66336, SU-101, UCN-01, Bay 43-9006, BMS-214662, CI-1040, GW572016, LErafAON, LY-317615, perifosine, phenoxodiol, PKI 166, swainsonine, 17-AAG, decitabine, CI-994, depsipeptide, MG98, phenylbutyrate, phenylacetate, suberoylanilidehydroxamic acid, Adp53, antineoplastons, A10/AS2-1, OL(1) p53, p53, RPR/INGN-201, SCH 58500, HSV-TK VPC, tgDCC-E1A, INX3280, TK gene pioglitazone, troglitazone, BAY12-9566, BMS-275291, clodronate, Marimastat, prinomastat, MMI270, COL-3, CP-471,358, trans retinoic acid, bexarotene, pivaloyloxy-methylbutyrate, 9-cis-retinoic acid, 13-cis RA, Fenretinide, ILX23-7553, TAC-101, tazarotene, bevacizumab, RhuMab-VEGF, HuMV833, Angiozyme, IMC-1C11, PI-88, SU5416, CP547,632, PNU-145156E, PTK/ZK 787, SU6668, ZD6474, carboxyamidotriazole, GBC-590, squalamine, Vitxain, ABT-510, CM101, ZD6126, Neovastat, suramin, thalidomide, IM862, TNP-470, angiostatin, CC-5013, combretastatin A4, endostatin, interleukin-12, alemtuzumab, edrecolomab, epratuzumab HuM195, oregovomab, rituximab, Ch14.18, MDX-11, WX-G250, 3F8, H22xKI-4, ING-1, J591, KM871, immunoconjugates antibody with toxin, BL22, Anti-Tac-PE38 (LMB-2), BB-10901, SS1-PE38, denileukin diftitox (ONTAK), IL13-PE38QQR, TP-38, Allovectin-7, 105AD7, BEC2, TriGem, 1A7, 3H1, vaccines, MDX-H210, G17DT, MDX-447, EMD 273063, IL-2/histamine, LAK, TIL, CTL, Bay 50-4798, MDX-010, OK-432, PSK, ubenimex, GM-CSF, ONYX-015, NV1020, PV701, Reolysin, celecoxib, Lyprinol, LY293111, astrasentan, melatonin, taurolidine, cyclosporin A, verapamil, tirapazamine trastuzumab, clodronate, trans retinoic acid, edrecolomab, rituximab, OK-432, ubenimex, melatonin, PSC 833, R115777, ZD1839, SCH 66336, decitabine, HSV-TK, VPC, BAY12-9566, Marimastat, prinomastat, suramin, 105AD7, IL-2/histamine, astrasentan.

In order to stretch the coating to an adequate extent, it is often sufficient for at most every other of adjacent, continuous openings in the predetermined section of the main structure to be covered or spanned by the at least one pharmaceutically active substance.

A particularly simple design of the implant, in particular for stents, is attained by composing the main structure of closed cells or meshes, wherein each cell comprises a continuous opening. Preferably each cell is formed by two or more struts that may be bent and/or curved.

It is advantageous when the material of the coating that contains the pharmaceutically active substance is elastic. Preferably, the material of the coating has a modulus of elasticity in the range 0.01 kN/mm$^2$ to 4 kN/mm$^2$, preferably in the range 0.01 kN/mm$^2$ to 2 kN/mm$^2$. The extensibility or elasticity of the material of the coating is 100% to 800%, preferably 300% to 800%. It is therefore possible to dilate the implant without damaging the coating.

Furthermore, it is advantageous that the elution (delivery) of the pharmaceutically active substance begins more rapidly in certain regions of the coating, e.g. in the center of a coating of an opening, than in other regions, due to the material of the coating being stretched as a result of dilation, for example. It is thereby ensured that the pharmaceutically active substance is released over an extended period of time and is not washed out entirely as soon as treatment starts. These kinetics can be controlled by way of the dilation, which is defined by the mechanics of the main structure, and the design of the coating.

It is furthermore preferable for the coating to contain at least one polymer from the group containing the polymers of the class of elastomers, in particular rubber and latex, furthermore containing PET (polyethylene terephthalate), PS (polystyrene), PA (polyamide), PUR (polyurethane), PE (polyethylene), PES (polyethersulfone), PTFE (polytetrafluorethylene, TEFLON), PLA (polylactide, polylactic acids), PLLA (poly-L-lactide), PLGA (poly-L-glycolide), PGA (polyglycolide), PBMA (poly-butyl-methacrylate), PEVA (polyethylene vinyl acetate), memory-effect polymers, and the blends, copolymers and block polymers thereof. Examples of polymers having memory effect are multiblock copolymers or standard polymers (PET, PS, PUR, PE, PES, PTFE). The stated polymers are particularly well suited to absorbing a pharmaceutically active substance in highly diverse forms and to delivering it at the treatment site since these polymers are highly elastic and do not tear when stretched slightly. Furthermore, many of the stated polymers have the aforementioned properties in terms of the extensibility thereof since the implant is often dilated at the treatment site. Preferably the material of the coating is biocompatible and possibly also biodegradable.

Memory-effect polymers (FGP) are plastics that have a shape memory effect, that is, they can apparently "remember" their previous external shape despite having since been deformed to a significant extent. Such memory-effect polymers are typically composed of two components. The first is an elastic polymer, a type of "spring element". The second component is a hardenable wax which can lock the "spring element" into any desired shape after it hardens. If the memory-effect polymer is now heated, the wax softens and is therefore no longer able to counteract the force of the elastic polymer (first component). In this state, the memory-effect polymer returns to the (original) shape thereof. The aforementioned memory-effect polymers (FGP) are particularly well suited to absorbing a pharmaceutically active substance in highly diverse forms and delivering it at the treatment site since pores can be "programmed" into these polymers, which can be opened during and after dilation at the implantation site and thereby release the at least one pharmaceutically active substance. The provision or creation ("programming") of pores in the coating material containing at least one memory-effect polymer was explained above.

In a further embodiment, the coating which is designed as a layer or "skin" is connected to the main structure by way of an adhesive connection, a form-fit connection, and/or a bond (i.e. by way of a chemical bond), e.g. the coating containing the pharmaceutically active substance is attached to the struts which form the main structure. In one embodiment, the main structure of the implant, preferably a part of the struts, therefore comprises a groove for the attachment of the coating, preferably on the abluminal side.

The main structure of such an implant can contain preferably at least one element and/or compound of the following group composed of metals, metal alloys, preferably stainless steel, CoCr, magnesium alloys, iron alloys, zinc alloys, manganese alloys, Nitinol, polymers from the class of biodegradable polymers, preferably polylactic acids, poly-caprolactone, blends or copolymers thereof, polymers from the class of biocompatible polymers, preferably UHMWPE and PEEK. In that particular case, an implant designed as a stent composed of a biodegradable magnesium alloy, iron alloys, zinc alloy, or manganese alloy is referred to as AMS (=absorbable metal stent).

The position of a stent is often determined using imaging methods e.g. using an x-ray device. Since the materials used for the matrix lattice of stents typically absorb x-rays only to a low extent, i.e. they are x-ray lucent or radiolucent, the implant in one embodiment of the invention is equipped with at least one x-ray marker which contains a material that absorbs x-rays to a greater extent (also referred to as x-ray opaque or radiopaque material) than the surrounding material. The x-ray opaque material is contained in the coating preferably in liquid form e.g. a pure iodine. In that case, the liquid, x-ray opaque material is processed together with the material of the matrix during the coating process. It hardens at a later point in time or becomes solid in another manner and is present in solid form after completion of the coating process i.e. in the stent, which has been crimped into position, or in the stent that has been inserted into the body and may have been dilated. Alternatively, the x-ray opaque material can be present in encapsulated form. In that case the material of the microcapsule is biocompatible and non-resorbable. The x-ray opaque material can include e.g. gold, silver, or tantalum particles. The microcapsules preferably have a size of 0.5 μm to 1 μm.

Such an x-ray marker comprises x-ray opaque material, namely one or more of the elements and/or compounds from the group containing gold, platinum, silver, tungsten, iodine, tantalium, yttrium, niobium, molybdenum, ruthenium, rhodium, barium, lanthanum, cerium, praseodymium, neodymium, samarium, europium, gadolinium, terbium, dysprosium, holmium, erbium, thulium, ytterbium, lutetium, hafnium, rhenium, osmium and bismuth, and an x-ray opaque compound of these elements, in particular the complexes thereof, when they are present in salt form, and barium sulfate, bismuth trioxide, bromine, iodine, iodide, ionic iodine-containing compounds (such as amidotrizoic acid, trade names: GASTROLUX, GASTROGAFIN, PERITRAST), non-ionic, iodine-containing compounds (such as compounds having the trade names ULTRAVIST, ISOVIST, XENETIX), gaseous carbon dioxide ($CO_2$), titanium oxide, and zircon oxide.

The problem described above is furthermore solved by a system composed of a catheter having a balloon and an implant, wherein the implant is described above and the implant is disposed on the balloon of the catheter. Such a system is well-suited for inserting the implant having the above-described advantages for treatment into an organism.

The problem described above is also solved by a method for manufacturing an implant, which has the following steps:
  providing a main structure which has a large number of continuous openings,
  applying a coating which, in the dilated state, covers at least 20% of the cross-sectional area, preferably at least 50% of the cross-sectional area, of at least a portion of the openings in a predetermined section of the main structure—preferably the openings in the predetermined section having the smallest area—and releases at least one pharmaceutically active substance.

The above-described method according to the invention is a simple method for manufacturing an implant according to the invention.

As discussed above, the coating is preferably applied by covering at most every other of the adjacent, continuous openings in the predetermined section with the coating which releases at least one pharmaceutically active substance. Particularly preferably the coating is applied such that at most 95% of the sum of the cross-sectional areas of all openings in the predetermined section is covered or spanned by the coating that releases the at least one pharmaceutically active substance in the dilated state.

It is furthermore advantageous for the coating to be applied by way of immersion, dipping, spraying, pipetting, or the like, wherein the areas not to be coated can be protected by a resist and/or a covering.

In a preferred embodiment of the manufacturing process according to the invention, the coating is applied first, and then pores are formed in the coating, preferably in a stretched state of the coating, or pores are broken open, and the at least one pharmaceutically active substance is applied into the pores while or after the pores are formed or broken open. As a result, the pharmaceutically active substance is released from the coating particularly after the implant has been dilated. Furthermore, the direction into which the at least one pharmaceutically active substance is delivered can be easily controlled.

The problem described above is also solved by a method for manufacturing a system composed of a catheter and an implant, wherein the implant is first manufactured as described above, and the implant is then attached to the catheter, preferably on the balloon of the catheter, e.g. being crimped thereon. This manufacturing process is economical.

The method according to the invention, the implant according to the invention, and the system according to the invention are described in the following in examples, with reference to FIGs. All of the features described and/or depicted graphically form the subject matter of the invention, also independently of their combination in the claims or their back-references.

DESCRIPTION OF THE DRAWINGS

In the drawings, the following depict schematically.

DETAILED DESCRIPTION

Figure 1:
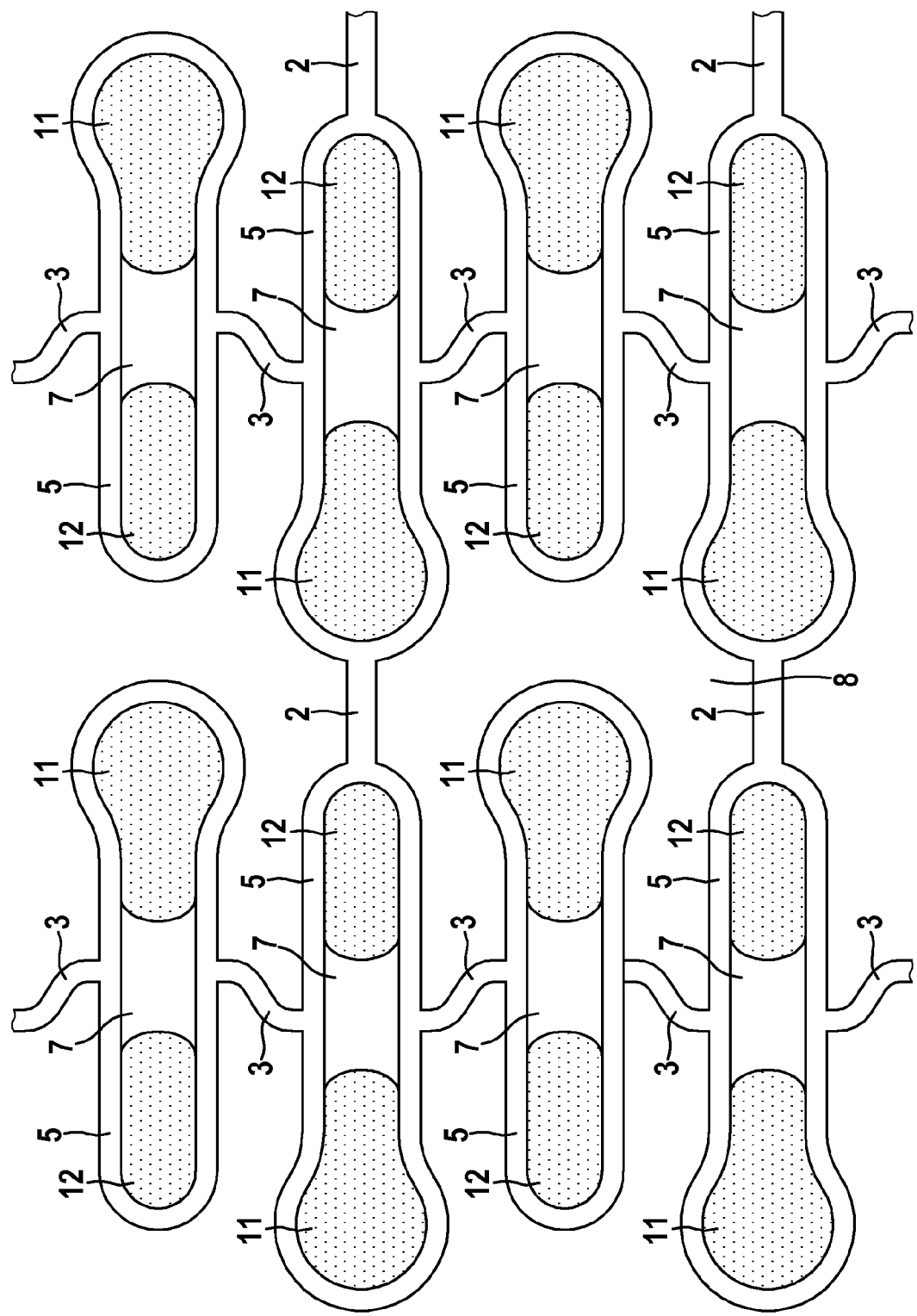
FIG. 1 a section of a first embodiment of an implant according to the invention, in a view from the side
FIG. 2 a section of a second embodiment of an implant according to the invention, in a view from the side,
FIG. 3 a section of a third embodiment of an implant according to the invention, in a view from the side,
FIG. 4 a section of a fourth embodiment of an implant according to the invention, likewise in a view from the side,
FIG. 5 a view of a cell of an implant according to the invention, with a coating, in a view from the side,
FIG. 6 a section of a fifth embodiment of an implant according to the invention, in a view from the side, in a non-dilated state (FIG. 6a) and in a dilated state (FIG. 6b), and
FIG. 7 a cross section of a cell of the embodiment of an implant according to the invention as depicted in FIG. 5.

The section of a main structure of a hollow cylindrical stent, which is shown in FIG. 1, comprises straight struts 2 extending in the longitudinal direction, and struts 3 curved in the shape of an "S" which extend transversely to the longitudinal direction on the jacket surface. Two curved struts 5 are disposed between two struts 2 extending in the longitudinal direction and two struts 3 curved in the shape of an "S", which in combination form an approximately keyhole-shaped, continuous opening 7. Struts 2 which extend in the longitudinal direction are disposed only in every other longitudinally-extending row of meshes formed by struts 5. A mesh or cell is formed by the two struts 5 which form keyhole-shaped opening 7. In addition, the combination of six curved struts 5, two diametrically opposed, straight struts 2, and four struts 3 curved in the shape of an "S" form one mesh or cell having an "H"-shaped opening 8. The cross-sectional area of keyhole-shaped opening 7 is smaller than the cross-sectional area of "H"-shaped opening 8.

Keyhole-shaped openings 7 are covered over approximately 70% of their cross-sectional area by a coating containing at least one pharmaceutically active substance. The coating is composed of a materix material, in particular rubber, latex, PLLA (poly-L-lactide), PLGA (poly-L-glycolide) or PBMA (poly-butyl-methacrylate), or a memory-effect polymer. The coating furthermore comprises one or more pharmaceutically active substances, preferably paclitaxel or sirolimus. The pharmaceutically active substance(s) is/are released by being washed out by bodily fluid.

The coating shown in FIG. 1 comprises two parts: a first part 11 on the top end, and a second part 12 on the bottom end of each keyhole-shaped opening 7. "H"-shaped openings 8 are not spanned by a coating. Given this coating configuration, the quantity and concentration of active substance can be varied by way of the design and the variable filling density.

The main structure of the stent comprising struts 2, 3, and 5 is preferably composed of a metal alloy CoCr or, in a particularly preferred embodiment, of a biodegradable magnesium alloy.

Figure 2:
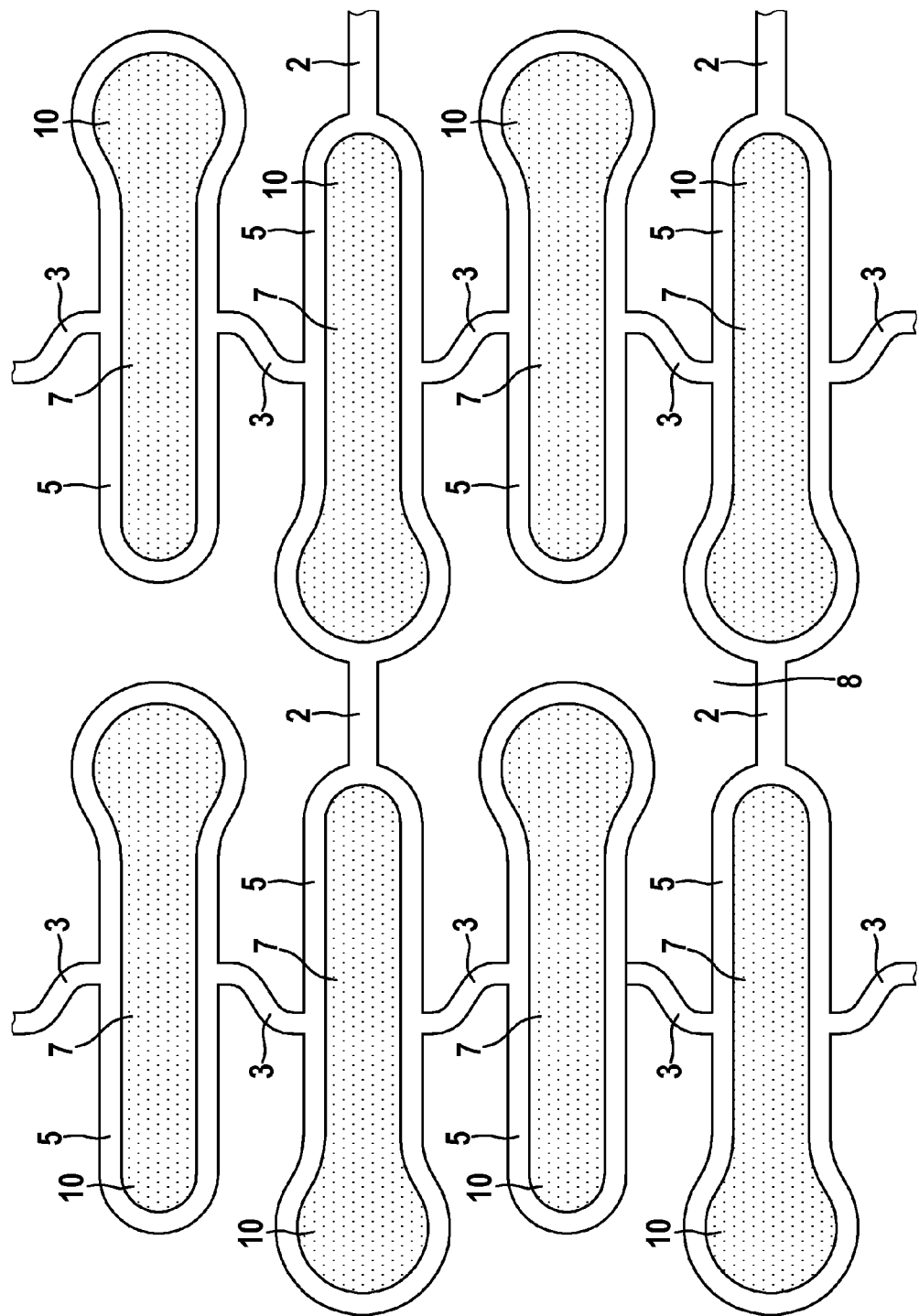

In the embodiment depicted in FIG. 2, 100% of the cross-sectional area of each keyhole-shaped opening 7 is covered with a coating 10. In addition to keyhole-shaped openings 7, the main structure of the stent also comprises "H"-shaped openings which are not covered with a coating containing the pharmaceutically active substance, similar to the embodiment shown in FIG. 1.

Likewise, in the embodiment shown in FIG. 3, the cross-sectional area formed by approximately oval openings 7' is covered by up to 100% with coating 10'. The approximately "H"-shaped openings 8', which are disposed therebetween and are formed by struts 2, 3', and 5', are not provided with a coating.

FIG. 4 shows a main structure of a stent according to the invention, which comprises approximately circular meshes formed by curved struts 5". Each approximately circular cross-sectional area of opening 7" of the meshes is covered completely with coating 10".

The approximately circular meshes are interconnected by struts 3' which extend transversely to the longitudinal direction. In this embodiment, no separate struts are disposed in the direction of the longitudinal direction of the stent. "H"-shaped meshes 8", which are formed by struts 3' and struts 5", do not have a coating.

Figure 5A:
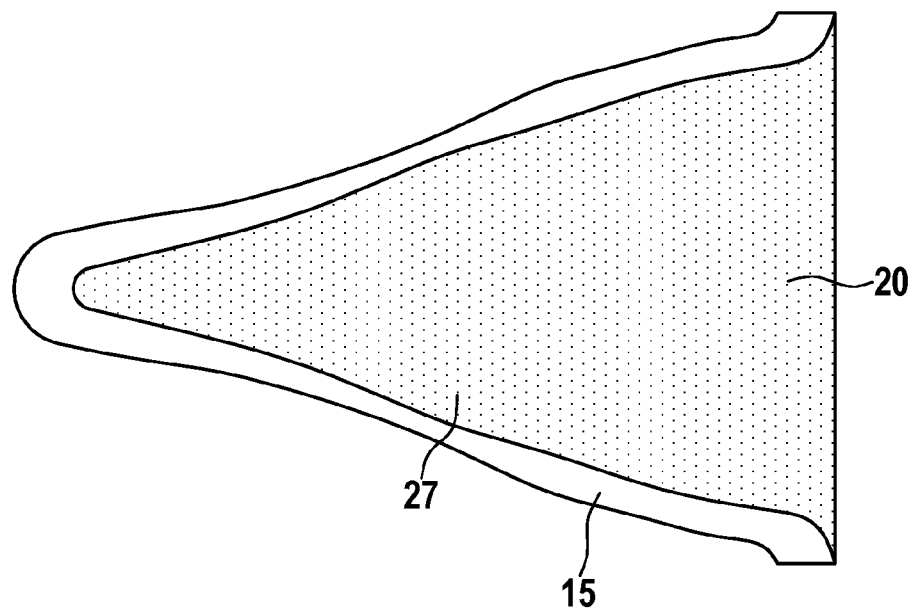
Figure 5B:
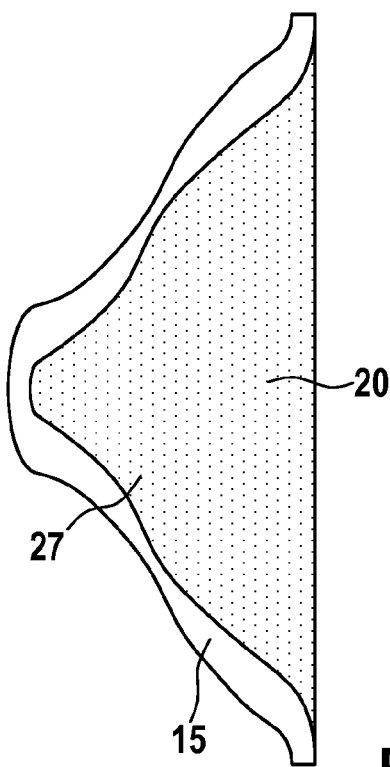

FIG. 5 shows the section of a strut 15, which forms a mesh or cell of the main structure of an implant according to the invention, in a view from the luminal direction. This strut is covered by a coating 20 containing at least one pharmaceutically active substance, which spans a continuous opening 27 formed by strut 15 in each case. Sections of the same meshes are shown in FIGS. 5a) and 5b), wherein strut 15 with coating 20 depicted in FIG. 5a) belongs to a non-dilated implant, while strut 15 shown in FIG. 5b) was dilated with the corresponding implant. Coating 20 is elastic and can therefore assume both states without tearing.

Figure 6A:
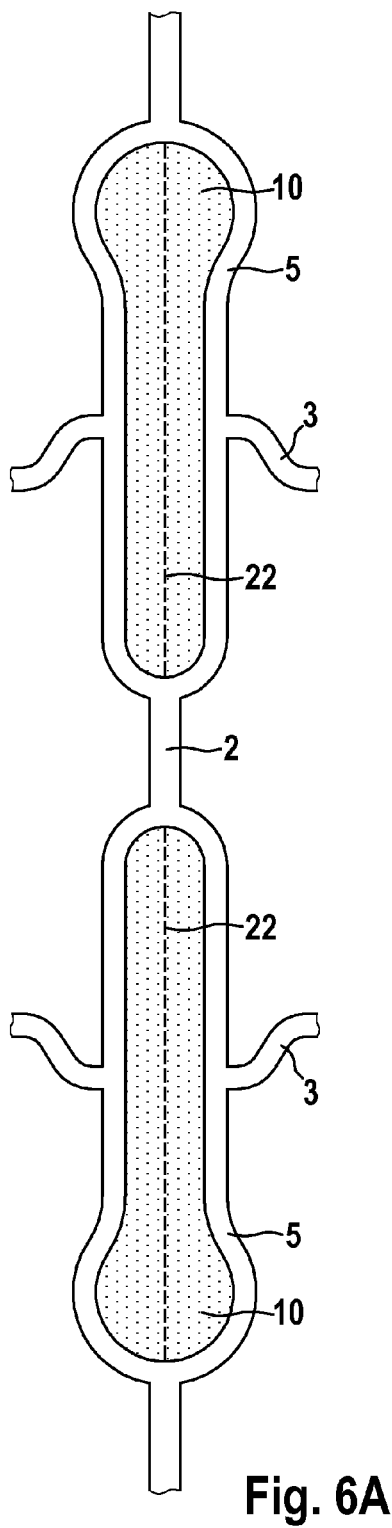
Figure 6B:
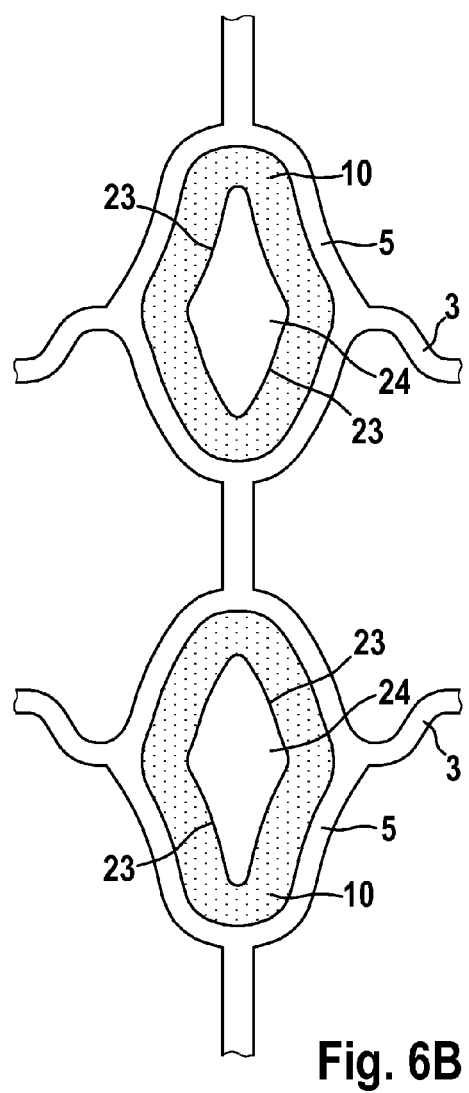

FIG. 6 shows a further embodiment of an implant according to the invention, which substantially corresponds to the embodiment shown in FIG. 2. The keyhole-shaped openings are disposed in the opposite direction compared to the second embodiment. Furthermore, coating 10 has a perforation line 22 extending approximately along a center line, which is indicated using a dashed line, is closed in the non-dilated state (see FIG. 6a)), and represents a predetermined breaking line. Interspaced holes are disposed in coating 10 and/or coating 10 has a slightly smaller layer thickness along perforation line 22. During dilation of the implant after placement thereof at the site in the body to be treated, the expansion of coating 10 is so great that perforation line 22 tears open and creates an opening 24. Opening 24 is enclosed by edges 23 which extend along perforation line 22 which was previously present i.e. in the non-dilated state. The tearing-open of coating 10 along a predetermined perforation line 22 during dilation has the advantage that opening 24 in coating 10 forms at a defined point. In addition, the tearing-open of coating 10 enables the pharmaceutically active substance(s) contained in coating 10 to be released.

Figure 7:
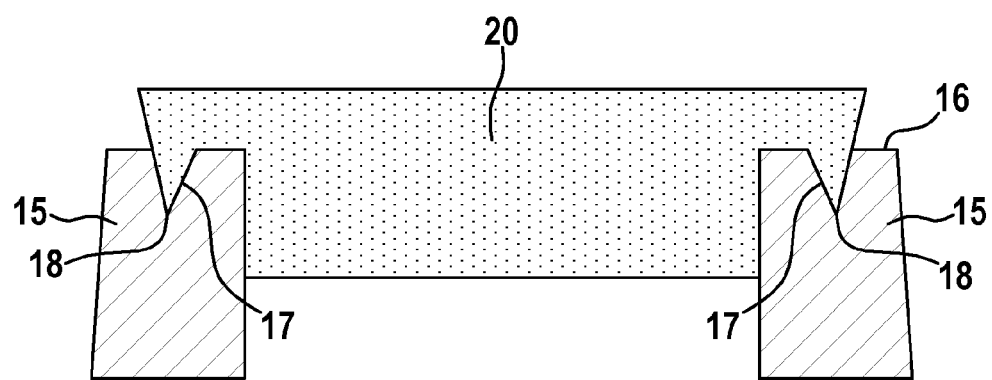

FIG. 7 shows a cross section of the embodiment depicted in FIG. 5. Coating 20 is anchored using grooves (slots) 17 formed by a laser and which are disposed on abluminal side 16 of respective strut 15. Coating 20 is affixed in grooves 17 using a form-fit connection and/or an adhesive (bonded connection) which is not depicted. Alternatively, a bonded connection between coating 20 and strut 15 can be attained without a groove. FIG. 5 shows the course of base line 18 of groove 17, which has a triangular cross section, as a dash-dotted line.

Coating 10, 10', 10", 11, 12 and 20 depicted in FIGS. 1 to 6 is used preferably as a highly elastic carrier of one or more pharmaceutically active substances. These substances can be introduced into the solution and, therefore, into the future polymer, simply by way of immersion or diffusion e.g. during manufacture of the coating solution. Furthermore, x-ray markers or x-ray opaque materials can also be provided in the coating. They can be embedded into the layer or the layer material e.g. using enclosed particles, or by way of immersion, diffusion, sputtering, or electrochemical or static deposition processes, possibly followed by heat treatment for introduction or fixation.

The coating is applied by dipping, spraying, pipetting, or the like, wherein the areas not to be treated are protected by a resist, a hydrophobic coating, and/or a covering.

In one embodiment, all of the areas or recesses (exposed areas) not to be coated are provided with a covering and/or a hydrophobic protective layer. The implant is then coated by way of immersion or dipping to form the coating which releases at least one pharmaceutically active substance. If the coating takes place from all sides in this step, the luminal side of the stent is covered in particular. The coating material does not adhere to the surfaces of the stent that were provided with the covering or protective layer. In the final step, the coverings or protective layers are removed by heating, stripping, or etching. The hydrophobic protective layer can remain on the struts if it is biocompatible.

Basically, the coating is not only deposited onto the struts, but also spans certain specific openings or a certain specific region of certain openings by forming the coating by pipetting in a targeted manner, if the aim is to not coat all openings. It is thereby ensured that all holding regions are utilized, as shown in FIG. 7. After the matrix hardens, voids can be formed in certain specific regions of the coating. Suitable methods therefor would be e.g. laser cutting, laser dotting, or making incisions. In a further embodiment, so-called predetermined breaking points can also be punched or rolled into the coating. The coating then tears open at exactly this point during dilation.

Memory-effect polymers can also be used in the coating. Any material that can be used to produce polymers can be used as the first element or main component. It is furthermore preferable for these materials to be biocompatible. The second element used to manufacture a memory-effect material induces the programming which is used to bring the plastic into its second, temporary shape. After the polymer has been manufactured for a certain field of application, it is processed in the classical manner. In that case, the material is melted and cooled once. The plastic is thereby given its first, permanent shape. Next, the material is reheated, in fact, beyond the so-called switching temperature thereof. This switching temperature results from the specific properties of the material and is based on a phase transition of the polymer chains, which is much lower than the original processing temperature. The plastic is thereby reshaped a second time, is cooled once more below the switching temperature and is thereby "programmed", i.e. locked into the second, temporary shape thereof. The coating is brought to the application site thereof in this shape. There, the material receives its specific thermal stimulus e.g. by way of the body temperature of the organism being treated or by way of a warm fluid that is brought to the polymer using a probe. This stimulus causes the polymer to reassume the first, permanent shape thereof at the treatment site. The aforementioned memory-effect polymers (FGP) are particularly well suited to absorbing a pharmaceutically active substance in highly diverse forms and to delivering it at the treatment site, since pores can be provided ("programmed") in these polymers, which can be opened after dilation at the implantation site and thereby release the active substance. The pharmaceutically active substance is added during or after the "programming". Examples of polymers having memory effect are multiblock copolymers or standard polymers (PET, PS, PUR, PE, PES, PTFE). The programming takes place e.g. by briefly heating the memory-effect polymer to the memory-effect temperature, which causes the polymer to expand. In this phase, pores can break open or be formed by way of punching or etching. The active substance can now be filled into the pores e.g. by diffusion.

The maximum layer thickness of the coating is preferably 100 μm. The required elasticity of the coating is not ensured if the layer thickness is greater than 100 μm.

The implants according to the invention are characterized in that a large area is created for the release of a pharmaceutically active substance. As a result, the active substance can be distributed more evenly in the region of the organ to be treated. The dosage of the active substance can therefore be increased. Furthermore, the distribution of the coating on various sections of the implant can be designed differently, e.g. differently on the proximal end or the distal end of the implant.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE CHARACTERS

2 Strut
3, 3' Strut
5, 5', 5" Strut
7 Keyhole-shaped opening
7' Oval opening
7" Circular opening
8, 8', 8", H"-shaped opening
10, 10', 10" Coating
11 Coating
12 Coating
15 Strut
16 Abluminal side
17 Groove
18 Base line
20 Coating
22 Perforation line
23 Edge
24 Opening
27 Opening

What is claimed is:

1. An implant having a cylindrical main structure formed by a plurality of closed cells, each cell having a continuous opening and connected to a neighboring cell in a circumferential direction by a connecting strut that does not form part of a cell and at least two of the cells joined longitudinally, wherein opposing halves of each of the plurality cells have a different internal area, characterized in that at least 20% of a cross-sectional area of the continuous opening of at least one cell in a predetermined section of the main structure is covered by a coating in a dilated state by spanning the coating across the cross-sectional area at opposing ends of the at least one cell and less than the entirety of each of the continuous openings is covered in the dilated state and at most 95% of the cross-sectional area of the sum of all continuous openings is covered in the dilated state, wherein the connecting strut that connects the at least one cell to its neighboring cell is not covered, wherein the coating is loaded with at least one pharmaceutically active substance and releases the at least one pharmaceutically active substance when in a dilated state.

2. The implant according to claim 1, characterized in that the at least one cell is a keyhole shaped cell.

3. The implant according to claim 2, wherein opposing ends of the keyhole shaped cell are covered by the coating and are separated by an opening that is not covered by the coating, wherein the continuous opening is about 70% covered.

4. The implant according to claim 1, characterized in that the pharmaceutically active substance is released from the coating at least primarily in the abluminal direction.

5. The implant according to claim 1, characterized in that the coating comprises a plurality of layers, wherein the first layer which is located furthest away in the luminal direction is a diffusion barrier for the at least one pharmaceutically active substance.

6. The implant according to claim 1, characterized in that the material of the coating has a modulus of elasticity in the range $0.01 \text{ kN/mm}^2$ to $4 \text{ kN/mm}^2$ or a modulus of elasticity in the range $0.01 \text{ kN/mm}^2$ to $2 \text{ kN/mm}^2$.

7. The implant according to claim 1, characterized in that the coating comprises at least one polymer that is a rubber or latex elastomer, which comprises at least one member selected from the group consisting of polyethylene terephthalate (PET), polystyrene (PS), polyamide (PA), polyurethane (PUR), polyethylene (PE), polyethersulfone (PES), polytetrafluoroethylene (PTFE), polylactide (PLA), poly-L-lactide (PLLA), poly-L-glycolide (PLGA), polyglycolide (PGA), poly butyl methacrylate (PBMA), polyethylene vinyl acetate (PEVA), a memory-effect polymer or a multiblock copolymer, and a blend, copolymer and block polymer thereof.

8. The implant according to claim 1, characterized in that the coating comprises at least one x-ray marker or a material for improving MRI visibility.

9. The implant according to claim 1, wherein every other cell along the circumferential direction is joined to another cell in a longitudinal direction by a longitudinal strut.

10. The implant according to claim 1, wherein the coating comprises a memory-effect polymer.

11. The implant according to claim 1, wherein about 70% of each of the continuous openings is covered.

12. A method for manufacturing an implant comprising the following steps:

forming a main structure having a plurality of closed cells, wherein opposing halves of each of the plurality cells have a different internal area, each cell having a continuous opening and connected to a neighboring cell in a circumferential direction by a connecting strut; and applying a coating comprising a pharmaceutically active substance for release such that at least 20% of the cross-sectional area of at least one cell in a predetermined section and in a dilated state is covered by spanning the coating across the cross-sectional area at opposing ends of the at least one cell and less than the entirety of each of the continuous openings is covered in the dilated state and at most 95% of the cross-sectional area of the sum of all continuous openings is covered in the dilated state, wherein the connecting strut that connects the at least one cell to its neighboring cell is not covered.

13. The method according to claim 12, characterized in that the coating is applied by immersion, dipping, or spraying, wherein the areas or area regions not to be treated are protected by a resist or a covering.

14. The method according to claim 12, characterized in that after the step of applying the coating, pores are formed in the coating or pores are broken open, and the at least one pharmaceutically active substance is applied into the formed or broken open pores.

15. A method for manufacturing a system composed of a catheter and an implant, wherein the implant is manufactured according to claim 12, and the implant is then fastened to the catheter or on a balloon of the catheter.

* * * * *